(12) United States Patent
Lindner (10) Patent No.: US 9,151,707 B2
(45) Date of Patent: Oct. 6, 2015

(54) METHOD FOR THE FUNCTIONAL CONTROL OF AN INSPECTION DEVICE AND DEVICE FOR THE INSPECTION OF A PRODUCT FLOW

(75) Inventor: Peter Lindner, Langquaid (DE)

(73) Assignee: KRONES AG, Neutraubling (DE)

( * ) Notice: Subject to any disclaimer, the term of this patent is extended or adjusted under 35 U.S.C. 154(b) by 254 days.

(21) Appl. No.: 13/884,285

(22) PCT Filed: Nov. 8, 2011

(86) PCT No.: PCT/EP2011/005606
§ 371 (c)(1),
(2), (4) Date: May 30, 2013

(87) PCT Pub. No.: WO2012/062449
PCT Pub. Date: May 18, 2012

(65) Prior Publication Data
US 2013/0271755 A1    Oct. 17, 2013

(30) Foreign Application Priority Data
Nov. 9, 2010  (DE) .......... 10 2010 043 632

(51) Int. Cl.
*G01N 21/00* (2006.01)
*G01N 21/90* (2006.01)
*G01N 21/93* (2006.01)
*G01N 21/88* (2006.01)

(52) U.S. Cl.
CPC ............... *G01N 21/00* (2013.01); *G01N 21/90* (2013.01); *G01N 21/93* (2013.01); *G01N 2021/8832* (2013.01)

(58) Field of Classification Search
CPC ............. G01N 2035/0408; G01N 2035/0465; G01N 21/17

USPC ............ 356/237.1–237.6, 240.1, 239.1, 356/239.3–239.8
See application file for complete search history.

(56) References Cited

U.S. PATENT DOCUMENTS 5,216,481 A * 6/1993 Minato ............ 356/239.1
5,459,313 A   10/1995 Schrader et al.

FOREIGN PATENT DOCUMENTS

| DE | 2166235 A1 | 7/1973 |
| DE | 3245908 A1 | 6/1984 |
| DE | 4302656 C1 | 5/1994 |
| DE | 4300169 A1 | 7/1994 |

(Continued)

OTHER PUBLICATIONS

International Search Report for PCT/EP2011/005606, dated May 3, 2012.

(Continued)

*Primary Examiner* — Gregory J Toatley
*Assistant Examiner* — Iyabo S Alli
(74) *Attorney, Agent, or Firm* — Marshall, Gerstein & Borun LLP (57) ABSTRACT

A method for checking an inspection device for a product flow, where the proper functioning of the inspection device can be checked even without using test containers specially provided for such checking, and having a radiation detector for measuring an inspection radiation after interacting with the products in order to detect a characteristic test radiation, and a further check is made as to whether the detected test radiation fulfills a target requirement characteristic of proper functioning of the inspection device.

23 Claims, 4 Drawing Sheets

(56) References Cited

FOREIGN PATENT DOCUMENTS

| DE | 19646678 A1 | 5/1998 |
|---|---|---|
| DE | 19646694 A1 | 5/1998 |
| DE | 10065321 A1 | 7/2002 |
| EP | 0491555 A1 | 6/1992 |
| WO | WO-02054050 A2 | 7/2002 |
| WO | WO-2005119224 A1 | 12/2005 |

OTHER PUBLICATIONS

German Search Report for Application No. 10 2010 043 632.1, dated Mar. 31, 2011.

\* cited by examiner

METHOD FOR THE FUNCTIONAL CONTROL OF AN INSPECTION DEVICE AND DEVICE FOR THE INSPECTION OF A PRODUCT FLOW

The invention relates to a method for the functional control of an inspection device for a product flow according to the preamble of claim 1 and a device for the inspection of a product flow according to the preamble of claim 15.

In beverage filling lines and comparable production units, container flows in different production stages are optically inspected. For example, the side wall and the bottom of the containers are inspected by imaging with the bright field method, while the mouth region of the containers is imaged with the dark field method. In contrast, the check for the presence of residual liquids, for example caustic solutions, is usually effected without imaging with the aid of infrared radiation or high-frequency radiation. For the functional control of the mentioned inspection devices, marked test containers are usually passed through the devices and it is checked whether test marks present on the test containers can be identified. However, this procedure, which is described, for example, in DE 4 302 656 C1, DE 19 646 694 A1, and WO 2005/119224 A1, involves several disadvantages:

For example, the test containers must always be kept in a perfect condition because apart from the mark of the test containers, in particular the test marks should be reliably identified. If this is not the case, the test result is falsified and/or the test procedure not completed. Moreover, tampering will be possible by purposefully changing test marks after a not successful test run to be able to continue production. Moreover, the mark of the test containers requires that the region of the mark be excluded from functional control. Further basic disadvantages are the safety risk for operators when the test containers are being inserted, for example when containers are filled with caustic solutions, and the required reduction of machine efficiency when the test containers are being inserted. Furthermore, such functional controls are usually only carried out every hour, so that in efficient plants, functional control takes place, for example, every 60000 containers. Thus, there remains a risk in that a high number of produced containers does not correspond to the required quality criteria between functional controls.

There thus is a need for a method for the functional control of inspection devices for product flows and for correspondingly improved inspection devices to avoid or at least attenuate the above mentioned disadvantages.

The set object is achieved with a method for the functional control of an inspection device according to claim 1. Accordingly, a characteristic test radiation is detected with a radiation detector for measuring an inspection radiation, and it is furthermore checked whether the detected test radiation fulfills a target requirement characteristic of proper functioning of the inspection device. Thus, the characteristic test radiation itself can contain characteristic information which are, instead of a test mark on a container to be checked, suited for checking a reaction to the characteristic test radiation expected at the radiation detector.

The characteristic test radiation is suited for checking the source of inspection radiation of an inspection beam path provided in the inspection device and/or the radiation detector. One can also check with the characteristic test radiation whether an evaluation unit and/or display unit provided at the inspection device reacts properly to the test radiation. For example, the characteristic test radiation can be changed in time to detect a crash of the evaluation system of the inspection device and/or a freezing of displayed screen contents.

The characteristic property of the test radiation can be any information that can be distinguished from system-related or environment-related fluctuations during normal operation of the inspection device, for example signal noise. Here, it is advantageous if the characteristic property of the test radiation simulates a soiling or damage of the containers that should be detected. The target requirement can be, for example, a certain parameter range, for example an intensity range of the detected test radiation, a time history of a measuring signal supplied by the radiation detector, or a predetermined spatial distribution of the test radiation in the region of the radiation detector.

Preferably, the characteristic test radiation differs from the inspection radiation with respect to its beam profile and/or its intensity of irradiation. The test radiation can be understood, for example, as modulation of the inspection radiation, where the inspection radiation and the test radiation interact with the containers to be checked and the inspection beam paths essentially in the same manner. Thereby, soiling or damages can be particularly reliably detected. In other words, it is an advantage if the inspection radiation and the characteristic test radiation have the same wavelength, cover the same wavelength range, or the wavelength ranges of the two radiations at least overlap.

In a preferred embodiment, the characteristic test radiation is weaker than the inspection radiation. Thereby, a situation where the inspection radiation is weakened by water drops, fog or mist, vapor or any other soiling of the inspection beam path can be simulated in a simple manner, so that no reliable detection of defective containers is possible. Moreover, one can check in a simple manner whether the inspection device reacts to signal changes in general.

Preferably, the characteristic test radiation is guided through an inspection beam path of the inspection device that must be checked. Thereby, the transmission behavior of the inspection beam path can be checked. One can determine, for example, whether the inspection beam path is inadmissibly affected by vapor, fog or mist, or whether a refractive optical element located in the beam path, for example a protecting glass, is soiled or damaged.

In a preferred embodiment, the radiation detector detects the characteristic test radiation in the running product flow if no product is located in the inspection beam path. In particular inspection devices with bright field illumination can be checked thereby without test containers. Thus, neither any test container where a test mark is attached, nor any test container where a test mark is temporarily generated by projection and reflection or transmission of a test pattern is required. Thus, functional control can be performed between two containers each of the production flow. Consequently, no containers must be marked as test containers and sorted out from the production flow. Thereby, functional control can be performed particularly reliably and with a particularly low influence of the production procedure.

In a further preferred embodiment, the characteristic test radiation is directed onto a product located in the inspection beam path. One can thereby generate a temporary mark on the product to be inspected even with dark field illumination, for example in the form of a characteristic signal or a characteristic test pattern, to simulate a defective product. Thus, the product flow can also continue in normal production operation during functional control. In particular, the insertion of special test products in the production flow can be eliminated.

Preferably, the product irradiated with the characteristic test radiation is then designated as test object. Since a defect is simulated with the test radiation, a proper functional control with the test radiation will lead to the product irradiated with the test radiation being discharged. The marking of the product irradiated with the test radiation permits an identification of the product as test object with the aim of an unambiguous allocation of discharged products.

Preferably, the product marked as test object is used as test object for at least one further inspection of the product flow. Thereby, the number of test objects required for the functional control can be reduced altogether with the aim of reducing costs for the functional control.

In a particularly advantageous embodiment, the characteristic test radiation is detected by imaging, and the characteristic target requirement is the presence of a characteristic test feature in an image detected with the aid of the test radiation. Thereby, imaging inspection methods can also be reliably checked.

Preferably, the test feature is an image contrast which is characteristic of a damage or soiling of the product, or a malfunction of the inspection device. Thereby, different sources of defects can be easily simulated in imaging detection. Thus, a particularly practical function test can be performed.

In a particularly advantageous embodiment, the beam profile of the characteristic test radiation has characteristic bright/dark transitions, in particular bright/dark transitions in the form of lines and/or patterns. With imaging detection, defect criteria that can be particularly easily and reliably checked can be generated thereby. For example, line grids or rasters can be highly reliably distinguished from system-related interfering components, such as image noise, and adapt to actually occurring sources of defects as to their size. For example, the resolution of bright/dark grids could be adjusted to the required resolution in defect detection. For example, the distance between adjacent bright/dark transitions could correspond to the extent of damages or soiling to be detected of the products to be checked.

In an advantageous embodiment, the position of the bright/dark transitions is changed in the beam profile of the characteristic test radiation, and at least one test image is taken before, and one test image after the change. The test images are moreover compared to each other. Thereby, inspection devices can be checked in particular where moving structures must be detected, for example in impurity detection in filled bottles. It would be also possible to only change a part of the bright/dark transitions in the beam profile and to leave other regions of the bright/dark transitions constant. Thus, a situation can be simulated as it is also present in impurity detection in filled bottles. Here, the impurities moving in the bottle must be distinguished from a stationary ribbing of the bottle's bottom or the like. The comparison of the test images permits at least two snapshots which must differ in at least one characteristic feature when the inspection device is functioning properly.

When the characteristic target requirement is missed, a production stop and/or a cleaning process are preferably triggered. This permits an automation of inspection and functional control, so that the probability of defective production and the duration of production interruptions due to a production stop or cleaning process are minimized.

In a particularly advantageous embodiment, it is furthermore verified whether the product has been discharged from the product flow as a consequence of the functional control. This can additionally increase the reliability of functional control.

The set object is furthermore achieved with a device for inspecting a product flow according to claim 15. Accordingly, the device according to the invention comprises a function test device for providing a characteristic test radiation to be detected with the radiation detector and for checking whether the detected test radiation fulfills a target requirement characteristic of proper functioning of the inspection device.

Preferably, the radiation detector is a camera, and the function test device comprises an image evaluation unit which is suited for checking the presence of a test feature in an output image of the camera exposed to the test radiation. Such a configuration is suited for the functional control of all imaging inspection devices for product flows, where in particular the use of test products with permanently attached test features can be eliminated.

In an advantageous embodiment, the function test device comprises a production device for projecting a bright/dark pattern onto a diffusion screen or light shade provided in an inspection beam path on the illumination side. Thereby, one can provide characteristic information, in particular in imaging detection with the aid of an additional radiation source which could, for example, also be retrofitted, in order to simulate soiling of products or a damage of the inspection device.

Preferably, the function test device comprises a raster-like illumination field for generating a bright/dark illumination pattern, where the illumination field is in particular part of the inspection radiation source. Such illumination fields, as for example light emitting diode fields, or monitors permit a particularly flexible generation of test patterns in the form of bright/dark transitions. For example, several different patterns could be generated in one inspection cycle to check different criteria or image regions.

The function test device preferably comprises an adjustable attenuation device for attenuating or blocking the inspection radiation to provide a portion of the inspection radiation as test radiation. The attenuation device could be, for example, a mechanical shutter, a filter, an electronic shutter, such as an LCD field, or a controlling system for changing the brightness and/or the on and off time and/or current control of the inspection radiation source. Thereby, the function of the inspection device can be checked in a particularly simple manner, for example in the non-imaging check for determining residual liquid in a container. One could also check the time of the step response. This means that, if the radiation source has been activated, for example, for 100 µs, the response of the recorder should take place within a predetermined time range.

In a particularly advantageous embodiment, the device is a rotary machine which comprises several circulating inspection stations for inspecting one product each with a respective allocated radiation detector. In such inspection devices, the formerly common provision of special test objects is particularly complicated as all inspection stations must be equipped with such test objects for functional control. Thus, the problem solution according to the invention where such test objects can be eliminated is then particularly advantageous.

Preferably, the device is configured to carry out a functional control with the aid of the radiation detector provided for the pending inspection before each inspection of a container. Thereby, one can achieve a particularly high reliability of functional control and quality control.

Preferably, the device according to the invention comprises a radiation source which is designed such that it can generate both the inspection radiation and the test radiation. Thereby, a particularly compact and flexible inspection device can be provided. Moreover, the inspection beam path can be particularly reliably checked.

A particularly advantageous embodiment of the device according to the invention furthermore comprises a discharge device for discharging defective products and a checking device for checking whether a product has been discharged by the discharge device as a consequence of the functional control. Thereby, the reliability of functional control can be increased. The discharge device and the checking device can be in particular included in a request and verification master system for functional control which can initiate individual functional controls, for example depending on an event or within routine procedures, and which manages and evaluates feedback about the successful discharge of products on the basis of the functional control.

Preferred embodiments of the invention are represented in the drawing. In the drawings.

Figure 1A:
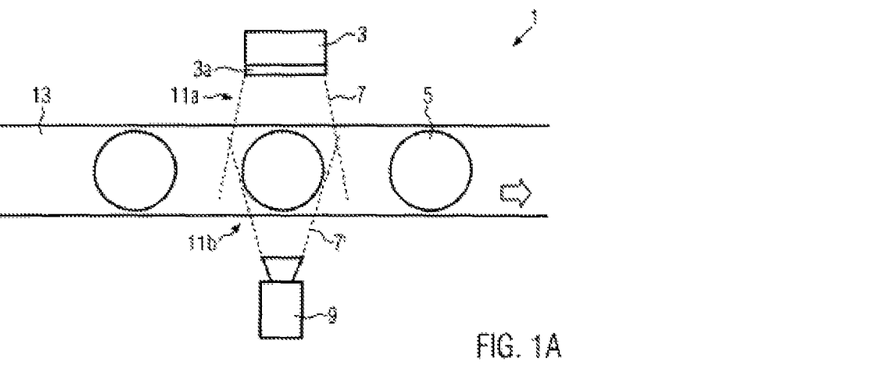
FIG. 1A shows a schematic plan view onto a first embodiment of the inspection device according to the invention with lateral transmitted illumination.
Figure 1B:
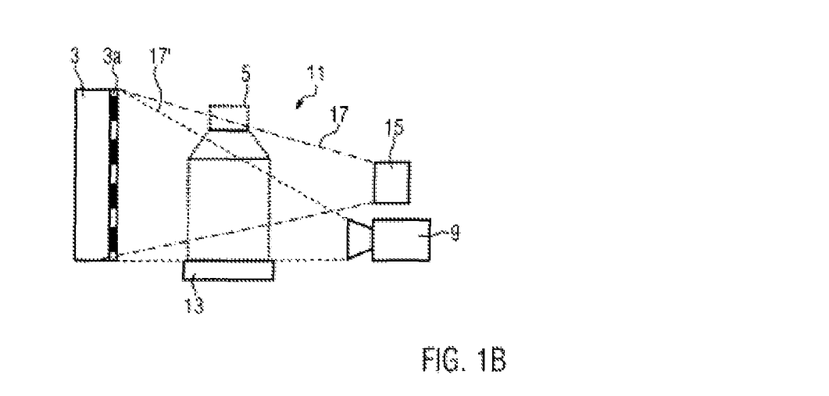
FIG. 1B shows a cross-section through the inspection device of FIG. 1A.

As one can see in FIG. 1, a first embodiment 1 of the inspection device according to the invention for checking a product flow, in particular a container flow, comprises an inspection radiation source 3 for illuminating containers 5 and the like with transmitted light with an inspection radiation 7, and a radiation detector 9 for measuring the inspection radiation 7' after interaction with the container 5. Between the inspection radiation source 3 and the radiation detector 9, an inspection beam path 11 is formed which comprises a section 11a on the illumination side and a section 11b on the detection side. In FIG. 1A, a transport device 13 for guiding the containers 5 through the inspection device 1 as a continuous product flow is indicated for the sake of good order. The inspection radiation 7 is, for example, light, but for certain applications it can also be electromagnetic high-frequency radiation. Below, the inspection radiation source 3 will also be designated as illumination device, depending on the described application.

In FIG. 1B, a test illumination device 15 which directs a test radiation 17 onto a diffusion screen 3a provided at the illumination device 3 is furthermore indicated. The radiation detector 9 is arranged such that it can detect a portion 17' of the test radiation 17 reflected by the diffusion screen 3a when there is no container 5 in the inspection beam path 11. In FIG. 1B, the container 5 is therefore only indicated by dotted lines. The beam paths of the above-mentioned radiations 7, 7', 17 and 17' are here only indicated schematically without restricting the invention to certain imaging variants, aperture angles or the like.

The test illumination device 15 is embodied such that it can project a test radiation 7 with characteristic bright/dark courses onto the diffusion screen 3a. Suited bright/dark courses are e.g. stripe patterns, bright/dark rasters, geometric figures, such as circles or polygons, dot patterns and the like. Bright/dark courses where the distance between bright and dark regions corresponds to a desired resolution in the detection of damages or soiling at the containers 5 to be inspected are advantageous.

The radiation detector 9 is preferably a camera, such as a CCD camera. The depth of field of the camera is then preferably selected such that a container surface to be inspected is imaged as sharply as the diffusion screen 3a with a test pattern projected onto the latter. As will be described more in detail below, however, a non-imaging radiation detector 9 would in principle also be conceivable.

The containers 5 are preferably transparent bottles or the like. The inspection radiation 7 is, for example, visible or infrared light. The illumination device 3 is, for example, an arc lamp, a laser, a light emitting diode or a light emitting diode field, an LED, LCD or OLED monitor or the like, with or without diffusion screen, to provide a plane, uniformly illuminated light source for inspection.

The test illumination device 15 preferably emits in the same spectral range as the inspection illumination device 3. However, it would also be conceivable that the spectral ranges of the inspection illumination device 3 and the test illumination device 15 only overlap in a spectral range relevant for the inspection of the containers 5. It is in general desirable that the inspection radiation 7, 7' and the test radiation 17, 17' enter into the same interactions with possible sources of interference in the beam path 11, such as water drops, vapors and fog or mist. This ensures that an attenuation of the test radiation 17, 17' by fog, mist or vapors will come close to a situation in the inspection of the containers 5.

An advantage of the transmitted light arrangement of the first embodiment 1 resides in the fact that the transmission properties of the inspection beam path 11 for the inspection radiation 7, 7' can be checked in the bright field even without the presence of a test container in the inspection beam path 11. This is permitted in particular by the fact that with the aid of the diffusion screen 3a or with another backscattering and/or reflecting optical element in the inspection beam path 11, a test radiation 17' with a characteristic property is generated which causes, with a proper function of the inspection device 1, a characteristic reaction of the radiation detector 9. For the imaging inspection of containers, test patterns in the form of bright/dark transitions in the beam profile of the test radiation 17' are particularly suited as characteristic property as in this manner, different measuring tasks of the container inspection can be simulated flexibly. The presence of the respective characteristic reaction of the radiation detector 9 thus represents a target requirement for confirming the perfect function of the inspection device 1. The principle of detecting a characteristic test radiation 17, 17' will be illustrated more in detail with reference to FIGS. 2A and 2B by way of example.

Figure 2A:
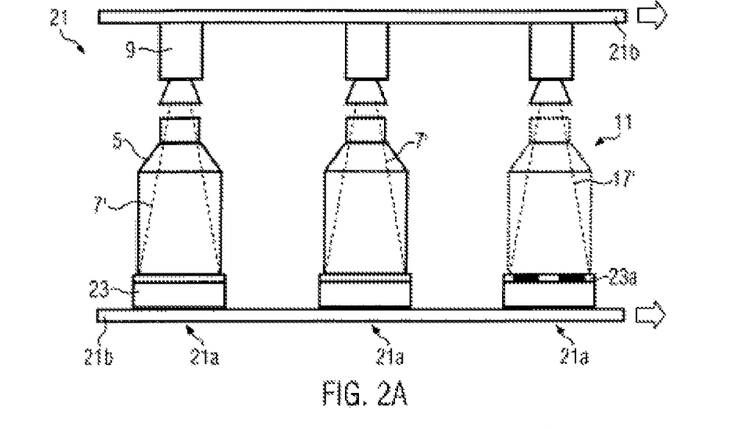
FIG. 2A shows a schematic lateral partial view of a second embodiment of the inspection device according to the invention with transmitted illumination from the bottom.

FIG. 2A shows a second embodiment 21 of the inspection device according to the invention for checking containers 5. The inspection device 21 comprises several identical inspection stations 21a which move together with the containers 5 to be inspected during inspection. For example, the inspection stations 21a can continuously circulate at a frame 21b as is indicated in FIG. 3C for a rotary-type inspection device 21.

At each inspection station 21a, an illumination device 23 and a radiation detector 9, preferably a camera, are provided for measuring the inspection radiation 7'. In the example of FIG. 2A, the illumination device 23 illuminates a container 5 to be inspected with transmitted light from the bottom, so that the bottom 5a of the container 5 can be detected by imaging by a camera 9 disposed above the container 5.

The inspection device 21 of FIG. 2A is, for example, a device for detecting impurities 5b in filled containers 5. In this case, the containers 5 are rotated before the imaging inspection in a section of the inspection device 21 provided upstream, and they are slowed down again just before inspection, so that the container's contents with possibly present impurities 5b moves with respect to the container 5 which is at rest relative to the camera 9.

Figure 2B:
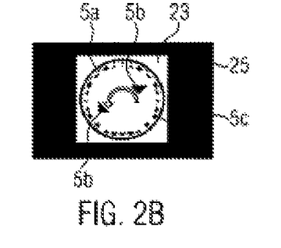
FIG. 2B shows a schematically shown inspection camera image of a container bottom to be inspected, taken with the device of FIG. 2A.

In FIG. 2B, an inspection camera image 25 is indicated with the illustration of a container bottom 5a with a stationary ribbing 5c over the illumination device 23 and an impurity 5c moving relative to it. The detection of impurities 5b is usually effected by comparing several inspection camera images 25 of the same container 5 which are taken one after another, whereby differences between the individual inspection camera images then only result from the moving impurities 5b.

Figure 2C:
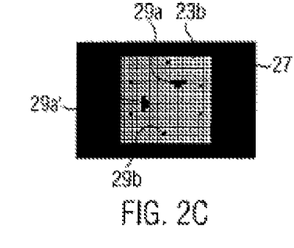
FIG. 2C shows a schematically shown test camera image of a screened illumination device with test features for checking the inspection device of FIG. 2A.

FIG. 2C shows a corresponding test camera image 27 of the camera 9 for the functional control of the inspection device 21, where there is no container 5 in the inspection beam path 11. The illumination device 23 is, in the example of FIG. 2A, embodied as raster-like light source, for example as light emitting diode field with a diffusion screen 23a, or as a display screen which permits to eliminate the diffusion screen 23a due to its high number of matrix dots. Analogously to the first embodiment is designated with 17', the test radiation after it has penetrated the diffusion screen 23a. However, a separate test illumination device is dispensable in the second embodiment 21 because the illumination device 23 can generate both the inspection radiation 7 and the test radiation 17, 17'. However, the invention is not bound to certain methods for generating, projecting or scattering the originally generated test radiation 17.

The individual luminescent dots 23b of the illumination device 23 can be selectively switched on and off. This permits to alternatively use the illumination device 23 as inspection illumination device and as test illumination device. To this end, the individual illumination dots 23b of the illumination device 23 are switched on or off to generate characteristic features 29a, 29b in the form of bright/dark differences in the test image 27 of the camera 9. In the example of FIG. 2C, these characteristic features 29a, 29b are indicated as relative minimal brightness by dark screen dots. The characteristic features 29a, 29b, however, could equally be regions with relative maximal brightness. Suitably, individual matrix dots 23b of the illumination device 23 are switched on or off in such a manner that the characteristic features 29a, 29 at least approximately correspond to impurities 5b to be detected in the inspection image 25 as to their sizes and/or distribution in the test camera image 27. Here, arbitrarily shaped and arranged test features 29a, 29b in the test image 27 are conceivable, depending on the number of luminescent dots 23b of the illumination device 23.

To simulate moving impurities 5b, it is, for example, possible to generate, one after another, at least two different bright/dark test patterns for the functional control of one inspection station 21a each in the test radiation 17, 17' and to compare the test camera images 27 respectively associated with the test patterns to each other. Here, it would be conceivable to change the positions of individual characteristic test features 29a, while other characteristic test features 29b remain unchanged and could thus simulate stationary structures of the test object, for example a ribbing 5c of a container bottom 5a. This is summarized in FIG. 2C, for the sake of simplicity in one single test camera image 27, with the characteristic feature 29a in a first position and a corresponding characteristic feature 29a' in a second position. In practice, the first feature 29a would be generated for taking a first test camera image 27, and the second feature 29a' for taking a second test camera image 27'. Of course, it would be possible to change or leave unchanged the positions of an arbitrary number of characteristic features 29a, 29b to simulate certain structures at the bottom of the container 5. It would also be possible to compare more than two test images 27, 27' with each other to check the inspection device 21 with respect to the characteristic target requirement.

For functional control, the period between two successive container inspections of the same inspection station 21a is essentially suited, that means between equipping the respective inspection station 21a and withdrawing the checked container 5. This period could be utilized for an arbitrary number of test camera images 27, 27' as long as the taking, storage and/or evaluation of the test camera images 27, 27' is done before the next container 5 to be checked is inserted into the respective inspection station 21a. This becomes clear with reference to FIG. 2D which shows a rotary-type inspection device 21 according to the invention with an incoming region 21c for the containers 5 to be checked and an outgoing region 21d for the checked containers 5. The functional control of the inspection stations 21a can thus be accomplished without restricting the machine efficiency in each case in a region 21e after the outgoing region 21d has been passed and before the incoming region 21c has been reached. The described functional control with a test radiation with at least one characteristic feature 29a, 29b is of particular advantage precisely for inspection stations 21a that run along and otherwise have to be simultaneously equipped with special test bodies for the functional control. As a characteristic property of the test radiation 17, 17', defined gradations of the test beam performance or characteristic radiation pulses are also possible, also with non-imaging detection.

In the first and second embodiments of the inspection device according to the invention, the containers 5 to be inspected are inspected in the bright field. Consequently, one advantage of the described functional control is exactly that no container 5 is required in the inspection beam path 11 for the functional control. Thus, the functional control of the inspection beam path 11 can be carried out between two successive inspections each as long as no container 5 is in the beam path 11. This permits, in an ideal case, a continuous functional control of the inspection device 1, 21. A control unit (not represented) could to this end continuously change between an inspection program and a program for functional control. Cameras 9 could be operated at twice the image-taking rate compared to conventional container inspection.

The functional control according to the invention is suited for various bright-field inspection methods, for example the bottom control of containers 5, the internal wall control of the containers 5, the side wall control of the containers 5, the detection of impurities 5b, and the detection of undesired residual liquid in the containers 5. This could be, for example, a caustic solution or oil.

The detection of residual liquid is usually not done by imaging, but rather in particular with the aid of infrared or high-frequent electromagnetic radiation. Since the detection of residual liquid is normally determined by an attenuation of the inspection radiation 7 when it penetrates the container 5, a characteristic test radiation 17 with an intensity of irradiation reduced by a known degree, for example by 50 to 90%, compared to the inspection radiation 7, is in particular suited for the functional control of such residual liquid detection. For example, the intensity of the test radiation 17 could at least approximately correspond to the intensity of irradiation to be expected when residual liquid is present in a container 5 to be checked. One can thereby check in a simple manner whether the radiation detector 9 reacts suitably within the measuring range relevant for container inspection. However, it would also be possible to provide a test radiation 17 with an increased intensity of irradiation compared to the inspection radiation 7.

The functional control according to the invention primarily facilitates the checking of the inspection beam paths 11. However, the correct function of the radiation detector 9 and the corresponding evaluation units and indicating instruments can be also checked. For example, successive functional controls with differing characteristic test radiations 7 could be performed. As a characteristic target requirement, differing measuring signals of the radiation detector 9 would then be conceivable. If such a target requirement is not reached, one could, for example, conclude that a crash of the evaluation system or a defective freezing of a screen display has occurred.

Just in the detection of residual liquids, a functional control of the inspection device 1, 21 without additional test body is of particular advantage. The handling of hazardous substances, such as caustic test solutions, which is potentially dangerous for the operators, is eliminated. Moreover, the need for providing test containers or comparable test bodies with reliably constant properties is eliminated. Moreover, the possibilities of tampering the functional control, in particular by changing the test bodies, are reduced or excluded.

Figure 3A:
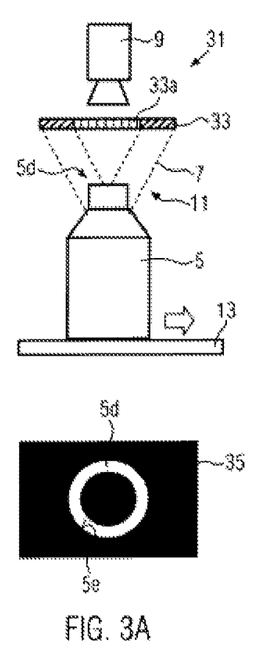
FIG. 3A shows a schematic side view of a third embodiment of the dark field inspection device according to the invention with a schematized inspection camera image.

FIG. 3A shows a third embodiment 31 of the inspection device according to the invention which operates according to the dark-field principle, in contrast to the aforementioned embodiments. An inspection device 31 for checking the mouth region 5*d* of a container 5 by imaging is represented by way of example. The illumination device 33 is annular and arranged diagonally above the mouth region 5*d*, so that the mouth region 5*d* can be checked with the aid of a camera 9 provided above the mouth region 5*d* through the annular illumination device 33.

The illumination device 33 comprises several circumferential sections 33*a* which can be selectively switched on and off. In the inspection of a container 5, preferably all circumferential partial segments 33*a* are switched on simultaneously to achieve a circumferentially uniform illumination of the mouth region 5*d* of the container 5. Damages or soiling of the mouth region 5*d* cause, in the inspection image 35 of the third embodiment 31, a bright/dark contrast 5*e* which can be identified due to its asymmetry with respect to the circumferentially uniformly illuminated mouth region 5*d*.

Figure 3B:
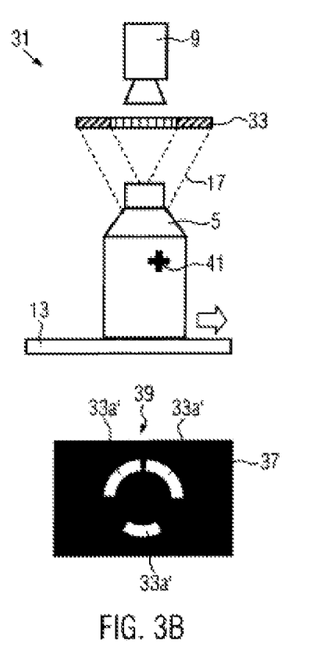
FIG. 3B shows a schematic side view of the third embodiment with a schematized test camera image.

On the basis of dark field illumination, no functional control of the inspection device of the third embodiment 31 can be performed without a container 5 in the inspection beam path 11. However, it is possible to image, instead of a specially prepared test container, a regular container 5 to be checked in the inspection position with the camera 9 by vertical illumination. To simulate a damage or soiling of the mouth region 5*d*, selected segments 33*a* of the inspection illumination device 33 can be switched on or off to generate an asymmetric illumination of the mouth region 5*d*. This is schematically indicated in FIG. 3B. In the example, only three segments 33*a*' are switched on for the functional control of the inspection device 31. Correspondingly, in the test camera image 37 indicated in FIG. 2B, three circumferential segments of the mouth region 5*d* are shown to be bright, and three circumferential segments are shown to be dark. Thus, in this embodiment 31, too, at least one characteristic feature in the form of a characteristic bright/dark transition is generated in the test image 37, for example in the form of dark circumferential segments.

It will be understood that, depending on the segmenting of the illumination device 33, different characteristic bright/dark transitions would be possible with the inspection device 31. It is decisive that at least one bright/dark transition is generated in a defined image region of the test image 37. This ensures that a characteristic feature 39 can be evaluated, where the target requirement is missed when the characteristic feature is not present in the test image 37 and one can assume a malfunction of the inspection device 31. For example, the inspection beam path 11 could be affected by a crack in the protecting glass or in the camera's optical system, vapor, fog or mist, drops of water on the CCD, on filter devices and/or protecting glasses, such that the contrast in the inspection image 35 required for detecting a damage 5*e* or soiling of the mouth region 5*d* cannot be ensured. Thus, a characteristic bright/dark transition missing in the test image 37 simulates an erroneously negative defect detection in the inspection of a soiled or damaged mouth region 5*d*.

The above described embodiments have in common that, when the functional control fails, preferably a production stop is caused, and/or a cleaning procedure is initiated with a preceding production unit.

The procedure when the functional control is passed, however, largely differs in that in the third embodiment 31, the container 5 irradiated with the test radiation 17 is detected as defective when the functional control has been passed and is sorted out from the production flow. Compared to this, the function test in the first and second embodiments is done without container 5, so that a passed function test does not influence the container flow. In particular, no container 5 must be discharged from the production flow in this case.

In the third embodiment 31, it is therefore desirable to minimize the number of containers 5 to be discharged in the functional control. To this end, the containers 5 can be identified by a suited mark 41, such as a transponder. For example, a container 5 could be designated with the mark 41 as test container after a function check has been performed, and for a subsequent functional control, it could be used again as a test container. It would also be possible to primarily use containers 5 which have been detected as defective in other quality tests for the described function tests. Thereby, containers 5 which have already been identified as defective containers, for example with a soiling on the side wall, can be used as test containers for a subsequent bottom or sealing surface control to reduce the number of containers 5 altogether required for functional control. Although a certain minimum rejection of containers 5 for the functional control of the third embodiment 31 cannot be avoided, none the less the need for having to store special test containers or similar test bodies of constant quality is eliminated. Here, too, the risk of tampering can be reduced and the flexibility of the function test can be increased with an only low affection of the product flow. If, however, an arbitrary non-marked container 5 would be used for the functional control of the third embodiment 31, the reason for the subsequent discharge of the container 5, i.e. the successful functional control, would no longer be reproducible. The container 5 could then not be distinguished from defective containers on a discharge conveyor belt. The mark 41 or an equivalent designation is therefore particularly advantageous for the operation of the third embodiment.

The described inspection devices 1, 21, 31 and the respective allocated methods for the functional control have in common that a test radiation 17, 17' with a characteristic property is directed onto the radiation detector 9 to permit its functioning and/or the permeability at least of a section of the respective inspection beam path 11. Such characteristic properties are, in particular with imaging detection, bright/dark distributions in the camera image to be evaluated. These are preferably caused by suited characteristic bright/dark distributions in the beam profile of the test radiation 17, 17'. Such a bright/dark distribution is possible, for example, by a projection of a bright/dark pattern onto a diffusion screen, a light shade or a structure limiting the inspection beam path. Such bright/dark distributions can equally be caused by plane radiation sources. To this end, screen-like illumination devices, such as light emitting diode fields which are available, for example, with several hundreds of matrix dots, or TFT monitors or OLED monitors are particularly suited. Monitors are in particular also suited as an inspection illumination device 3 without diffusion screen. Characteristic features of the test radiation 17, 17' could also be generated by a variation of the intensity of illumination in time. Mechanical shutters, filters and/or LCD screens in the beam path 11 are conceivable.

The evaluation of the measuring signals of the radiation detector 9 is preferably accomplished by a central evaluation unit (not represented). The latter could compare the respective measured signals with stored characteristic values. This could be, for example, intensity values, intensity courses over time, or monitor patterns in the form of contrast gradations. With such comparative values, one can above all fulfill the measuring task of checking the transmission behavior of the inspection beam path 11. This is in particular achieved in that a given signal, for example a bright/dark gradation of the test radiation 17, is passed through the beam path 11 and it is checked whether the response of the detector 9 to the incident test radiation 17' corresponds to a response to be expected.

With the inspection devices 1, 21, 31 according to the invention, one can work as described below:

In the first embodiment 1, a continuous flow of containers 5 to be inspected is transported through the fixed inspection beam path 11 between the inspection illumination device 3 and the radiation detector 9 with the aid of the transport device 13. The containers 5 are passed through the inspection device 1 at a given distance with respect to each other. When the beam path 11 is passed, the containers are irradiated each with an inspection radiation 17' following a given inspection procedure, and, if a defect is detected, such as a soiling or damage of the container 5, they are discharged from the running production flow. Between two inspected containers 5 each, a test radiation 17' is directed through the inspection beam path 11 onto the radiation detector 9. If a given characteristic property of the test radiation 17' is detected by the test measuring signal supplied by the radiation detector 9, proper functioning of the inspection device 1 is determined, and an approaching following container 5 is examined with the inspection radiation 7. If a characteristic property provided in the test radiation 17' is in contrast not detected on the basis of the measuring result determined by the radiation detector 9, one assumes a malfunction of the inspection device 1, and the production flow is preferably interrupted. Equally, a cleaning of upstream production plants can be initiated. Here, it would be possible to direct the test radiation 17 onto the radiation detector 9 every time after a predetermined number of containers 5 has passed, for example after every second or fifth container 5.

Figure 2D:
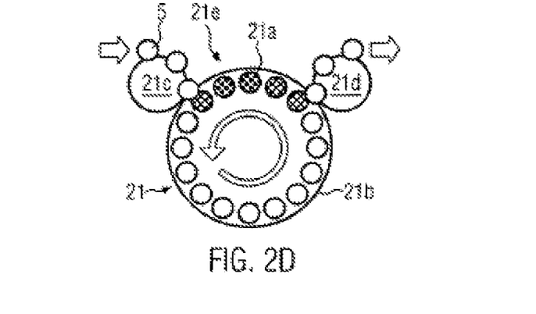
FIG. 2D shows a schematic plan view onto the second embodiment of the inspection device according to the invention with several circulating inspection stations.

In the second embodiment 21, the containers 5 to be inspected are each transferred to a circumferentially circulating inspection station 21a. Here, several inspection stations 21a are provided at a common inspection device 21, in particular a rotary one. The transfer of the containers 5 to the respectively allocated inspection station 21a and the discharge of the inspected containers 5 from the inspection device 21 are each accomplished in incoming and outgoing regions 21c, 21d, where the containers 5 are inspected after the inspection stations 21a have been equipped, while they are circulating around a circumferential segment of the inspection device 21. After the inspected containers 5 have been withdrawn, the inspection stations 21a are exposed to the test radiation 17, 17' in a partial section 21e where they are not equipped with a container 5, and the functional control of the inspection stations 21a is performed. Thus, all inspection stations 21a could be checked continuously, and in particular between two container inspections to be performed with the respective inspection station 21a, for their correct functions without having to reduce the machine efficiency of the inspection device 21.

In the third embodiment 31, preferably selected containers 5 are irradiated with the characteristic test radiation 17, and the reflected portion 17' of the test radiation 17 is evaluated with the camera 9. The selected containers are preferably marked as test containers. When the function test is successful, the selected container 5 is discharged from the product flow and preferably used for at least one further functional control in the production plant.

The described embodiments 1, 21, 31 can be combined in any technically reasonable manner. In particular, the characteristic test radiation 17, 17' can be generated both in fixed inspection devices and in inspection devices that go along with the containers 5 by different technical measures, such as projection, selective activation of grouped light elements, beam attenuation and the like. Here, imaging and non-imaging detections of the characteristic test radiation 17, 17' and the evaluation of different target requirements, for example the detection of characteristic bright/dark transitions or the measurement of an expected overall intensity of irradiation of the test radiation 17, 17', can be arbitrarily combined.

Figure 4:
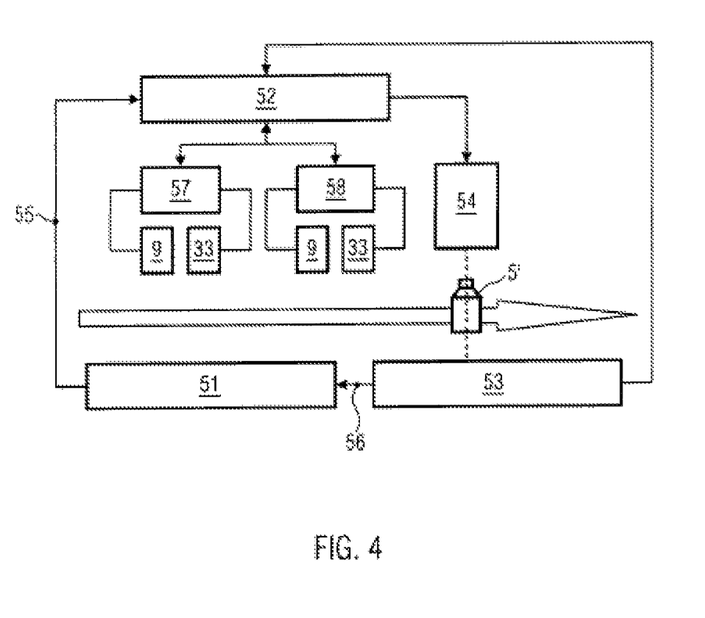
FIG. 4 shows a diagram of a central control system for requesting and verifying the functional control according to the invention.

The described embodiments 1, 21, 31 can moreover be connected to a master control system 51 for requesting and verifying functional control. This is advantageous in particular in combination with the third embodiment 31 where, as a consequence of a successful functional control, the container 5 is to be discharged by means of which the characteristic test radiation 17' was generated.

As shows FIG. 4, the control system 51 can be connected with a central control unit 52 of the inspection device 31 and with a counter control device 53. The latter is configured such that it can determine whether the container 5' associated with the functional control was actually discharged from the product flow by a discharge unit 54 associated with the inspection device 31. As FIG. 4 furthermore illustrates, the central control unit 52 receives at least one request signal 55 from the control system 51 for performing the function test and receives at least one feedback signal 56 from the counter control device 53 which can comprise, for example, a light barrier or a comparable detector for identifying the discharged container 5'. For the sake of good order, in FIG. 4 decentralized control units 57, 58 associated with the radiation detectors 9 and the inspection illumination devices 33 are moreover indicated.

Apart from an extensive verification of the functional control, the control system 51 could also be only used, for example, for sending test requests in the form of trigger signals 55 for the inspection illumination device 33 or the radiation detectors 9, or for switching over to suited test algorithms. One could also check, independent of the radiation detectors 9, whether the expected container 5' was actually discharged. Such a check could be inexpensively realized.

The described methods can also be carried out as a self-test function before the production start, as a cleaning check after production, and/or as a transfer test, e.g. in shift transfers.

The functional control is preferably logged, evaluated and/or stored by electronic data processing and/or by printout: for example associated by sequential numbers of the container and/or the batch, by a time stamp, an identification code and/or an event. The latter could be, for example, a manual test request, an automatically initiated test cycle, for example controlled by time, the number of containers, an event, e.g. the completion of a cleaning procedure of the system, or a purposeful predetermination of a certain test container. Possible evaluation parameters are, for example, target and actual values of contrast, brightness or result sums. The transfer of test results to guiding systems and/or mobile devices is also conceivable.

The contrast values could be used for readjusting the light sources and/or for subsequent focusing and/or for the adaptation of f-stops and exposure times.

The invention claimed is:

1. A method for the functional control of an inspection device for a product flow, comprising:
    activating an inspection device comprising at least one inspection radiation source to irradiate the products to be inspected with an inspection radiation,
    passing a characteristic test radiation that differs from the inspection radiation through an inspection beam path to be checked of the inspection device, and
    detecting the characteristic test radiation by imaging with a radiation detector for measuring the inspection radiation after interaction with the products and checking whether the detected test radiation fulfills a target requirement characteristic of proper functioning of the inspection device, and the target requirement characteristic is the presence of a characteristic test feature in an image detected with the aid of the test radiation,
    wherein the beam profile of the characteristic test radiation comprises a characteristic bright/dark transition,
    and wherein the characteristic test radiation is produced by at least one of a screen-like radiation source and a light projection onto a diffusion screen, a light shade or a structure limiting the inspection beam path.

2. A method according to claim 1, wherein the characteristic test radiation differs from the inspection radiation with respect to its beam profile and/or its intensity of irradiation.

3. A method according to claim 1, wherein the characteristic test radiation is weaker than the inspection radiation.

4. A method according to claim 1, wherein the radiation detector detects the characteristic test radiation while the product flow is running when no product is located in the inspection beam path.

5. A method according to claim 1, and directing the characteristic test radiation onto a product located in the inspection beam path.

6. A method according to claim 5, and marking the product irradiated with the characteristic test radiation as test object.

7. A method according to claim 6, wherein the product marked as test object is used as test object for at least one further inspection of the product flow.

8. A method according to claim 1, wherein the test feature is an image contrast which is characteristic of a damage or soiling of the product or a malfunction of the inspection device.

9. A method according to claim 1, and changing the position of the bright/dark transitions in the beam profile of the characteristic test radiation, and taking at least one test image before the change, and taking at least one test image after the change, and comparing the test images to each other.

10. A method according to claim 1, wherein, when the characteristic target requirement is missed, a production stop and/or a cleaning process is triggered.

11. A method according to claim 5, and verifying whether the product was discharged from the product flow as a consequence of the functional control.

12. A device for the inspection of a product flow, comprising:
    a radiation source for irradiating the products to be inspected with an inspection radiation,
    an inspection beam path for the inspection radiation,
    a radiation detector for measuring the inspection radiation after interaction with the products, and
    a function test device for providing a characteristic test radiation differing from the inspection radiation and to be detected with the radiation detector, and for checking whether the detected test radiation fulfils a target requirement characteristic of a proper function of the inspection device,
    wherein the radiation detector is a camera and the function test device comprises an image evaluation unit which is suited for checking the presence of a test feature in an output image of the camera exposed to the test radiation,
    and wherein the function test device comprises at least one of a screen-like radiation source and a projection device configured for projecting a characteristic bright/dark transition onto a diffusion screen, a light shade provided in the inspection beam path, or a structure limiting the inspection path, thereby directing the characteristic test radiation with a beam profile comprising the characteristic bright/dark transition through the inspection beam path.

13. A device according to claim 12, wherein the function test device comprises an adjustable attenuation device for attenuating or blocking the inspection radiation to provide a portion of the inspection radiation as test radiation.

14. A device-according to claim 12, wherein the radiation source is designed such that it can generate both the inspection radiation and the test radiation.

15. A device according to claim 12, wherein the function test device comprises a segmented illumination field with selectively activated light segments for generating a bright/dark illumination pattern.

16. A device according to claim 12, wherein the device is configured to perform, before each inspection of a container, a functional control with the aid of the radiation detector provided for the pending inspection.

17. A device according to claim 12, wherein the function test device comprises a projection device for projecting a bright/dark pattern onto a diffusion screen or light shade provided in an inspection beam path of the device on the side of illumination.

18. A device according to claim 12, wherein the device is a rotary-type device and comprises several circulating inspection stations for the inspection of one product each with a respectively associated radiation detector.

19. A device according to claim 12, and a discharge device for discharging defective products, and a control device for checking whether a product has been discharged by the discharge device as a consequence of functional control.

20. The method according to claim 1, wherein the product flow is a container flow.

21. The method according to claim 1, wherein the bright/dark transitions are in the form of lines and/or patterns.

22. The device according to claim 12, wherein the product flow is a container flow.

23. The device according to claim 15, wherein the illumination field is a component of the inspection radiation source.

* * * * *